US012600963B2

(12) United States Patent　　(10) Patent No.:　US 12,600,963 B2

Li et al.　　(45) Date of Patent:　Apr. 14, 2026

(54) DEPLETION OF ABUNDANT UNINFORMATIVE SEQUENCES

(71) Applicant: Tecan Genomics, Inc., Redwood City, CA (US)

(72) Inventors: Bin Li, Palo Alto, CA (US); Lin Pham, Belmont, CA (US)

(73) Assignee: Tecan Genomics, Inc., Redwood City, CA (US)

( * ) Notice: Subject to any disclaimer, the term of this patent is extended or adjusted under 35 U.S.C. 154(b) by 523 days.

(21) Appl. No.: 17/153,019

(22) Filed: Jan. 20, 2021

(65) Prior Publication Data

US 2021/0222162 A1　　Jul. 22, 2021

Related U.S. Application Data

(60) Provisional application No. 62/963,302, filed on Jan. 20, 2020.

(51) Int. Cl.
　　*C12N 15/10*　　　(2006.01)
　　*C12Q 1/6853*　　(2018.01)
(52) U.S. Cl.
　　CPC ....... *C12N 15/1096* (2013.01); *C12Q 1/6853* (2013.01)
(58) Field of Classification Search
　　CPC ........................... C12N 15/1096; C12Q 1/6853
　　　　　　　　(Continued)

(56) References Cited

U.S. PATENT DOCUMENTS

| 4,362,867 A | 12/1982 | Paddock |
| 4,458,066 A | 7/1984 | Caruthers et al. |

(Continued)

FOREIGN PATENT DOCUMENTS

| CA | 2444926 A1 | 11/2002 |
| CN | 1661102 A | 8/2005 |

(Continued)

OTHER PUBLICATIONS

Amos, 2000, DNA pooling in mutation detection with reference to sequence analysis, Am J Hum Genet 66:1689-1692.

(Continued)

*Primary Examiner* — Aaron A Priest
*Assistant Examiner* — Randi Lynn Beil
(74) *Attorney, Agent, or Firm* — Brown Rudnick LLP; Robert B. Ruh

(57)　　　　ABSTRACT

The use of different primer sets in reverse transcription incorporates tags allowing for the selective amplification of cDNA transcribed using the different primers. Primers targeting non-desired RNA sequences such as ribosomal RNA can be used to prevent subsequent amplification of cDNA transcribed from those non-coding fragments. Accordingly effective depletion of non-desired sequences after cDNA amplification can be achieved. Systems and methods of the invention have applications in whole-transcriptome analysis. Non-coding sequence targeting primers can include nucleotide analogs that, when enzymatically processed, prevent subsequent amplification. Library preparation can include single primer isothermal amplification (SPIA) techniques wherein an RNA sequence required for SPIA is included in random primers but is absent from primers targeting non-coding RNA.

10 Claims, 4 Drawing Sheets

(58) Field of Classification Search
USPC ........................................................ 506/26
See application file for complete search history.

(56) References Cited

U.S. PATENT DOCUMENTS

| | | | |
|---|---|---|---|
| 4,469,863 | A | 9/1984 | Ts'o et al. |
| 4,582,877 | A | 4/1986 | Fairchok et al. |
| 4,876,187 | A | 10/1989 | Duck et al. |
| 4,925,065 | A | 5/1990 | Golias |
| 4,935,357 | A | 6/1990 | Szybalski |
| 4,942,124 | A | 7/1990 | Church |
| 4,988,617 | A | 1/1991 | Andegren et al. |
| 4,996,143 | A | 2/1991 | Heller et al. |
| 5,011,769 | A | 4/1991 | Duck et al. |
| 5,034,506 | A | 7/1991 | Summerton et al. |
| 5,035,996 | A | 7/1991 | Hartley |
| 5,043,272 | A | 8/1991 | Hartley |
| 5,082,830 | A | 1/1992 | Brakel et al. |
| 5,090,591 | A | 2/1992 | Long |
| 5,130,238 | A | 7/1992 | Malek et al. |
| 5,169,766 | A | 12/1992 | Schuster et al. |
| 5,171,534 | A | 12/1992 | Smith et al. |
| 5,194,370 | A | 3/1993 | Berninger et al. |
| 5,216,141 | A | 6/1993 | Benner |
| 5,234,809 | A | 8/1993 | Boom et al. |
| 5,235,033 | A | 8/1993 | Summerton et al. |
| 5,242,794 | A | 9/1993 | Whiteley et al. |
| 5,312,757 | A | 5/1994 | Matsuyama et al. |
| 5,384,242 | A | 1/1995 | Oakes |
| 5,386,023 | A | 1/1995 | Sanghvi et al. |
| 5,399,491 | A | 3/1995 | Kacian et al. |
| 5,409,818 | A | 4/1995 | Davey et al. |
| 5,418,149 | A | 5/1995 | Gelfand et al. |
| 5,422,271 | A | 6/1995 | Chen et al. |
| 5,427,929 | A | 6/1995 | Richards et al. |
| 5,480,784 | A | 1/1996 | Kacian et al. |
| 5,494,810 | A | 2/1996 | Barany et al. |
| 5,508,169 | A | 4/1996 | Deugau et al. |
| 5,508,178 | A | 4/1996 | Rose et al. |
| 5,510,270 | A | 4/1996 | Fodor et al. |
| 5,525,471 | A | 6/1996 | Zeng |
| 5,545,522 | A | 8/1996 | Van Gelder et al. |
| 5,554,516 | A | 9/1996 | Kacian et al. |
| 5,554,517 | A | 9/1996 | Davey et al. |
| 5,556,752 | A | 9/1996 | Lockhart et al. |
| 5,565,340 | A | 10/1996 | Chenchik et al. |
| 5,573,913 | A | 11/1996 | Rosemeyer et al. |
| 5,578,832 | A | 11/1996 | Trulson et al. |
| 5,589,339 | A | 12/1996 | Hampson et al. |
| 5,602,240 | A | 2/1997 | De Mesmaeker et al. |
| 5,637,684 | A | 6/1997 | Cook et al. |
| 5,641,658 | A | 6/1997 | Adams et al. |
| 5,644,048 | A | 7/1997 | Yau |
| 5,665,549 | A | 9/1997 | Pinkel et al. |
| 5,667,976 | A | 9/1997 | Van Ness et al. |
| 5,667,979 | A | 9/1997 | Berrens |
| 5,679,512 | A | 10/1997 | Laney et al. |
| 5,681,726 | A | 10/1997 | Huse et al. |
| 5,683,879 | A | 11/1997 | Laney et al. |
| 5,688,648 | A | 11/1997 | Mathies et al. |
| 5,705,628 | A | 1/1998 | Hawkins |
| 5,708,154 | A | 1/1998 | Smith et al. |
| 5,710,028 | A | 1/1998 | Eyal et al. |
| 5,712,126 | A | 1/1998 | Weissman et al. |
| 5,716,785 | A | 2/1998 | Van Gelder et al. |
| 5,726,329 | A | 3/1998 | Jones et al. |
| 5,750,341 | A | 5/1998 | Macevicz |
| 5,759,822 | A | 6/1998 | Chenchik et al. |
| 5,763,178 | A | 6/1998 | Chirikjian et al. |
| 5,789,206 | A | 8/1998 | Tavtigian et al. |
| 5,824,517 | A | 10/1998 | Cleuziat et al. |
| 5,824,518 | A | 10/1998 | Kacian et al. |
| 5,837,832 | A | 11/1998 | Chee et al. |
| 5,876,976 | A | 3/1999 | Richards et al. |
| 5,882,867 | A | 3/1999 | Ullman et al. |
| 5,888,779 | A | 3/1999 | Kacian et al. |
| 5,888,819 | A | 3/1999 | Goelet et al. |
| 5,945,313 | A | 8/1999 | Hartley et al. |
| 5,952,176 | A | 9/1999 | McCarthy et al. |
| 5,958,681 | A | 9/1999 | Wetmur et al. |
| 5,965,409 | A | 10/1999 | Pardee et al. |
| 5,969,119 | A | 10/1999 | Macevicz |
| 5,972,618 | A | 10/1999 | Bloch |
| 6,004,744 | A | 12/1999 | Goelet et al. |
| 6,004,745 | A | 12/1999 | Arnold, Jr. et al. |
| 6,027,889 | A | 2/2000 | Barany et al. |
| 6,027,923 | A | 2/2000 | Wallace |
| 6,030,774 | A | 2/2000 | Laney et al. |
| 6,037,152 | A | 3/2000 | Richards et al. |
| 6,056,661 | A | 5/2000 | Schmidt |
| 6,077,674 | A | 6/2000 | Schleifer et al. |
| 6,087,103 | A | 7/2000 | Burmer |
| 6,090,553 | A | 7/2000 | Matson |
| 6,090,591 | A | 7/2000 | Burg et al. |
| 6,107,023 | A | 8/2000 | Reyes et al. |
| 6,110,709 | A | 8/2000 | Ausubel et al. |
| 6,150,112 | A | 11/2000 | Weissman et al. |
| 6,159,685 | A | 12/2000 | Pinkel et al. |
| 6,160,105 | A | 12/2000 | Cunningham et al. |
| 6,169,194 | B1 | 1/2001 | Thompson et al. |
| 6,172,208 | B1 | 1/2001 | Cook |
| 6,174,680 | B1 | 1/2001 | Makrigiorgos |
| 6,180,338 | B1 | 1/2001 | Adams |
| 6,190,865 | B1 | 2/2001 | Jendrisak et al. |
| 6,194,211 | B1 | 2/2001 | Richards et al. |
| 6,197,501 | B1 | 3/2001 | Cremer et al. |
| 6,197,557 | B1 | 3/2001 | Makarov et al. |
| 6,210,891 | B1 | 4/2001 | Nyren et al. |
| 6,225,109 | B1 | 5/2001 | Juncosa et al. |
| 6,225,451 | B1 | 5/2001 | Ballinger et al. |
| 6,232,104 | B1 | 5/2001 | Lishanski et al. |
| 6,251,639 | B1 | 6/2001 | Kurn |
| 6,262,490 | B1 | 7/2001 | Hsu et al. |
| 6,270,961 | B1 | 8/2001 | Drmanac |
| 6,280,935 | B1 | 8/2001 | Macevicz |
| 6,287,766 | B1 | 9/2001 | Nolan et al. |
| 6,287,825 | B1 | 9/2001 | Weissman et al. |
| 6,291,170 | B1 | 9/2001 | Van Gelder et al. |
| 6,306,365 | B1 | 10/2001 | Ruoslahti et al. |
| 6,306,597 | B1 | 10/2001 | Macevicz |
| 6,309,843 | B1 | 10/2001 | Timms |
| 6,326,142 | B1 | 12/2001 | Royer |
| 6,335,167 | B1 | 1/2002 | Pinkel et al. |
| 6,339,147 | B1 | 1/2002 | Lukhtanov et al. |
| 6,440,705 | B1 | 8/2002 | Stanton, Jr. et al. |
| 6,449,562 | B1 | 9/2002 | Chandler et al. |
| 6,582,938 | B1 | 6/2003 | Su et al. |
| 6,670,461 | B1 | 12/2003 | Wengel et al. |
| 6,686,156 | B2 | 2/2004 | Kurn |
| 6,692,918 | B2 | 2/2004 | Kurn |
| 6,770,748 | B2 | 8/2004 | Imanishi et al. |
| 6,777,180 | B1 | 8/2004 | Fisher et al. |
| 6,794,499 | B2 | 9/2004 | Wengel et al. |
| 6,815,164 | B2 | 11/2004 | Kurn |
| 6,815,167 | B2 | 11/2004 | Crothers et al. |
| 6,825,011 | B1 | 11/2004 | Romantchikov |
| 6,833,246 | B2 | 12/2004 | Balasubramanian |
| 6,849,404 | B2 | 2/2005 | Park et al. |
| 6,858,413 | B2 | 2/2005 | Kurn |
| 6,913,884 | B2 | 7/2005 | Stuelpnagel et al. |
| 6,917,726 | B2 | 7/2005 | Levene et al. |
| 6,924,104 | B2 | 8/2005 | Weissman et al. |
| 6,946,251 | B2 | 9/2005 | Kurn |
| 7,001,724 | B1 | 2/2006 | Greenfield |
| 7,033,764 | B2 | 4/2006 | Korlach et al. |
| 7,048,481 | B2 | 5/2006 | Sugata et al. |
| 7,052,847 | B2 | 5/2006 | Korlach et al. |
| 7,056,676 | B2 | 6/2006 | Korlach et al. |
| 7,056,716 | B2 | 6/2006 | Potter et al. |
| 7,060,441 | B2 | 6/2006 | Bourget et al. |
| 7,094,536 | B2 | 8/2006 | Kurn |
| 7,115,400 | B1 | 10/2006 | Adessi et al. |
| 7,170,050 | B2 | 1/2007 | Turner et al. |
| 7,175,982 | B1 | 2/2007 | McCarthy et al. |

(56)            References Cited

U.S. PATENT DOCUMENTS

| | | |
|---|---|---|
| 7,176,025 B2 | 2/2007 | Kurn et al. |
| 7,189,512 B2 | 3/2007 | Porat et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,273,730 B2 | 9/2007 | Du Breuil Lastrucci |
| 7,276,720 B2 | 10/2007 | Ulmer |
| 7,294,461 B2 | 11/2007 | Kurn |
| 7,300,755 B1 | 11/2007 | Petersdorf et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,351,557 B2 | 4/2008 | Kurn |
| 7,354,717 B2 | 4/2008 | Kurn |
| 7,361,466 B2 | 4/2008 | Korlach et al. |
| 7,361,468 B2 | 4/2008 | Liu et al. |
| 7,402,386 B2 | 7/2008 | Kurn et al. |
| 7,405,281 B2 | 7/2008 | Xu et al. |
| 7,414,117 B2 | 8/2008 | Saito et al. |
| 7,416,844 B2 | 8/2008 | Korlach et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,491,498 B2 | 2/2009 | Lapidus et al. |
| 7,501,245 B2 | 3/2009 | Quake et al. |
| 7,579,153 B2 | 8/2009 | Brenner et al. |
| 7,704,687 B2 | 4/2010 | Wang et al. |
| 7,741,463 B2 | 6/2010 | Gormley et al. |
| 7,771,934 B2 | 8/2010 | Kurn |
| 7,771,946 B2 | 8/2010 | Kurn |
| 7,803,550 B2 | 9/2010 | Makarov et al. |
| 7,846,666 B2 | 12/2010 | Kurn |
| 7,846,733 B2 | 12/2010 | Kurn |
| 7,867,703 B2 | 1/2011 | Sampson et al. |
| 7,939,258 B2 | 5/2011 | Kum et al. |
| 7,948,015 B2 | 5/2011 | Rothberg et al. |
| 7,985,565 B2 | 7/2011 | Mayer et al. |
| 8,017,335 B2 | 9/2011 | Smith |
| 8,034,568 B2 | 10/2011 | Kurn et al. |
| 8,053,192 B2 | 11/2011 | Bignell et al. |
| 8,071,311 B2 | 12/2011 | Kurn |
| 8,143,001 B2 | 3/2012 | Kur et al. |
| 8,209,130 B1 | 6/2012 | Kennedy et al. |
| 8,334,116 B2 | 12/2012 | Kurn |
| 8,465,950 B2 | 6/2013 | Kurn et al. |
| 8,492,095 B2 | 7/2013 | Kurn |
| 8,512,956 B2 | 8/2013 | Kurn |
| 8,551,709 B2 | 10/2013 | Kurn et al. |
| 8,852,867 B2 | 10/2014 | Kurn et al. |
| 8,999,677 B1 | 4/2015 | Soldatov et al. |
| 9,175,325 B2 | 11/2015 | Kurn et al. |
| 9,175,336 B2 | 11/2015 | Soldatov et al. |
| 9,181,582 B2 | 11/2015 | Kurn |
| 9,206,418 B2 | 12/2015 | Armour |
| 9,248,076 B2 | 2/2016 | Sullivan et al. |
| 9,546,399 B2 | 1/2017 | Amorese et al. |
| 9,650,628 B2 | 5/2017 | Amorese et al. |
| 9,702,004 B2 | 7/2017 | Van Eijk et al. |
| 9,745,627 B2 | 8/2017 | van Eijk et al. |
| 9,896,721 B2 | 2/2018 | Van Eijk et al. |
| 9,920,366 B2 | 3/2018 | Eltoukhy et al. |
| 10,036,012 B2 | 7/2018 | Amorese et al. |
| 10,102,337 B2 | 10/2018 | Scolnick et al. |
| 10,415,089 B2 | 9/2019 | Rava et al. |
| 10,457,995 B2 | 10/2019 | Talasaz |
| 10,570,451 B2 | 2/2020 | Salk et al. |
| 10,704,086 B2 | 7/2020 | Talasaz et al. |
| 10,738,364 B2 | 8/2020 | Talasaz |
| 2001/0000077 A1 | 3/2001 | Engelhardt et al. |
| 2001/0031739 A1 | 10/2001 | Dare |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0115088 A1 | 8/2002 | Kurn |
| 2002/0150919 A1 | 10/2002 | Weismann et al. |
| 2002/0155451 A1 | 10/2002 | Makrigiorgos |
| 2002/0164628 A1 | 11/2002 | Kurn |
| 2002/0164634 A1 | 11/2002 | Patil et al. |
| 2002/0197611 A1 | 12/2002 | Chagovetz |
| 2002/0197639 A1 | 12/2002 | Shia et al. |
| 2003/0017591 A1 | 1/2003 | Kurn |
| 2003/0022207 A1 | 1/2003 | Balasubramanian et al. |
| 2003/0049861 A1 | 3/2003 | Woodward |
| 2003/0082543 A1 | 5/2003 | Su et al. |
| 2003/0087251 A1 | 5/2003 | Kurn |
| 2003/0119150 A1 | 6/2003 | Ankenbauer et al. |
| 2003/0143555 A1 | 7/2003 | Bourget et al. |
| 2003/0175780 A1 | 9/2003 | Jones |
| 2003/0180779 A1 | 9/2003 | Lofton-Day et al. |
| 2003/0186234 A1 | 10/2003 | Kurn |
| 2003/0207279 A1 | 11/2003 | Crothers et al. |
| 2003/0211616 A1 | 11/2003 | Leong |
| 2003/0213905 A1 | 11/2003 | Lennon et al. |
| 2003/0215926 A1 | 11/2003 | Kurn et al. |
| 2003/0224439 A1 | 12/2003 | Lafferty et al. |
| 2003/0232348 A1 | 12/2003 | Jones et al. |
| 2004/0002371 A1 | 1/2004 | Paquin et al. |
| 2004/0005614 A1 | 1/2004 | Kurn et al. |
| 2004/0022689 A1 | 2/2004 | Wulf et al. |
| 2004/0023271 A1 | 2/2004 | Kurn et al. |
| 2004/0115815 A1 | 6/2004 | Li et al. |
| 2004/0137456 A1 | 7/2004 | Yokota et al. |
| 2004/0161742 A1 | 8/2004 | Dean et al. |
| 2004/0203019 A1 | 10/2004 | Kurn |
| 2004/0203025 A1 | 10/2004 | Kurn |
| 2004/0248153 A1 | 12/2004 | Dear et al. |
| 2005/0003441 A1 | 1/2005 | Kurn |
| 2005/0014192 A1 | 1/2005 | Kurn |
| 2005/0019793 A1 | 1/2005 | Kurn et al. |
| 2005/0059048 A1 | 3/2005 | Gunderson et al. |
| 2005/0064414 A1 | 3/2005 | Hanna |
| 2005/0064456 A1 | 3/2005 | Kurn |
| 2005/0123956 A1 | 6/2005 | Blume et al. |
| 2005/0136417 A1 | 6/2005 | Cole et al. |
| 2005/0142577 A1 | 6/2005 | Jones et al. |
| 2005/0191656 A1 | 9/2005 | Drmanac et al. |
| 2005/0191682 A1 | 9/2005 | Barone et al. |
| 2005/0208538 A1 | 9/2005 | Kurn et al. |
| 2006/0008807 A1* | 1/2006 | O'Hara .............. C12N 15/1003 435/6.14 |
| 2006/0008824 A1 | 1/2006 | Ronaghi et al. |
| 2006/0014182 A1 | 1/2006 | Kurn |
| 2006/0024678 A1 | 2/2006 | Buzby |
| 2006/0024711 A1 | 2/2006 | Apidus et al. |
| 2006/0035274 A1 | 2/2006 | Dong |
| 2006/0046251 A1 | 3/2006 | Sampson et al. |
| 2006/0051789 A1 | 3/2006 | Kazakov et al. |
| 2006/0068415 A1 | 3/2006 | Jones et al. |
| 2006/0134633 A1 | 6/2006 | Chen et al. |
| 2006/0216724 A1 | 9/2006 | Christians et al. |
| 2006/0263789 A1 | 11/2006 | Kincaid |
| 2006/0281082 A1 | 12/2006 | Zhu |
| 2006/0285430 A1 | 12/2006 | Seto |
| 2006/0286566 A1 | 12/2006 | Apidus et al. |
| 2006/0292597 A1 | 12/2006 | Shapero et al. |
| 2007/0031857 A1 | 2/2007 | Makarov et al. |
| 2007/0134128 A1 | 6/2007 | Korlach |
| 2007/0141604 A1 | 6/2007 | Gormley et al. |
| 2007/0224607 A1 | 9/2007 | Morgan et al. |
| 2007/0224613 A1 | 9/2007 | Strathmann |
| 2007/0231823 A1 | 10/2007 | McKernan et al. |
| 2007/0238122 A1 | 10/2007 | Allbritton et al. |
| 2007/0263045 A1 | 11/2007 | Okazawa |
| 2008/0038727 A1 | 2/2008 | Spier |
| 2008/0087826 A1 | 4/2008 | Harris et al. |
| 2008/0103058 A1 | 5/2008 | Siddiqi |
| 2008/0131937 A1 | 6/2008 | Schroeder |
| 2008/0160580 A1 | 7/2008 | Adessi et al. |

(56)        References Cited

U.S. PATENT DOCUMENTS

| | | | |
|---|---|---|---|
| 2008/0176311 A1 | 7/2008 | Kurn | |
| 2008/0182300 A1 | 7/2008 | Kurn | |
| 2008/0194413 A1 | 8/2008 | Albert | |
| 2008/0194416 A1 | 8/2008 | Chen | |
| 2008/0206764 A1 | 8/2008 | Williams et al. | |
| 2008/0213770 A1 | 9/2008 | Williams et al. | |
| 2008/0217246 A1 | 9/2008 | Benn et al. | |
| 2008/0241831 A1 | 10/2008 | Fan et al. | |
| 2008/0242560 A1 | 10/2008 | Gunderson et al. | |
| 2008/0286795 A1 | 11/2008 | Kawashima et al. | |
| 2009/0011959 A1 | 1/2009 | Costa et al. | |
| 2009/0024331 A1 | 1/2009 | Tomaney et al. | |
| 2009/0026082 A1 | 1/2009 | Rothberg et al. | |
| 2009/0029385 A1 | 1/2009 | Christians et al. | |
| 2009/0036663 A1 | 2/2009 | Kurn | |
| 2009/0061425 A1 | 3/2009 | Lo et al. | |
| 2009/0061439 A1 | 3/2009 | Buzby | |
| 2009/0068645 A1 | 3/2009 | Sibson | |
| 2009/0068655 A1 | 3/2009 | Williams | |
| 2009/0068709 A1 | 3/2009 | Kurn et al. | |
| 2009/0105081 A1 | 4/2009 | Rodesch et al. | |
| 2009/0117573 A1 | 5/2009 | Fu et al. | |
| 2009/0117621 A1 | 5/2009 | Boutell et al. | |
| 2009/0123923 A1 | 5/2009 | Yamamoto et al. | |
| 2009/0124514 A1 | 5/2009 | Fu et al. | |
| 2009/0127589 A1 | 5/2009 | Rothberg et al. | |
| 2009/0130721 A1 | 5/2009 | Kurn et al. | |
| 2009/0203085 A1 | 8/2009 | Kurn et al. | |
| 2009/0203531 A1 | 8/2009 | Kurn | |
| 2009/0233802 A1 | 9/2009 | Bignell et al. | |
| 2009/0233804 A1 | 9/2009 | Kurn et al. | |
| 2009/0239232 A1* | 9/2009 | Kurn | C12Q 1/6809 |
| | | | 506/26 |
| 2009/0275486 A1 | 11/2009 | Kurn et al. | |
| 2009/0280538 A1 | 11/2009 | Patel et al. | |
| 2009/0298075 A1 | 12/2009 | Travers et al. | |
| 2010/0015666 A1 | 1/2010 | Brenner et al. | |
| 2010/0021973 A1 | 1/2010 | Makarov et al. | |
| 2010/0022403 A1 | 1/2010 | Kurn et al. | |
| 2010/0029511 A1 | 2/2010 | Raymond et al. | |
| 2010/0069250 A1 | 3/2010 | White, III et al. | |
| 2010/0081174 A1 | 4/2010 | Dunn | |
| 2010/0105052 A1 | 4/2010 | Drmanac et al. | |
| 2010/0113296 A1 | 5/2010 | Myerson | |
| 2010/0129879 A1 | 5/2010 | Ach et al. | |
| 2010/0137143 A1 | 6/2010 | Rothberg et al. | |
| 2010/0159559 A1 | 6/2010 | Kurn et al. | |
| 2010/0167954 A1 | 7/2010 | Earnshaw et al. | |
| 2010/0173394 A1 | 7/2010 | Colston, Jr. et al. | |
| 2010/0203597 A1 | 8/2010 | Chen et al. | |
| 2010/0267043 A1 | 10/2010 | Braverman et al. | |
| 2010/0273219 A1 | 10/2010 | May et al. | |
| 2010/0311066 A1 | 12/2010 | Kurn | |
| 2010/0323348 A1 | 12/2010 | Hamady et al. | |
| 2011/0009276 A1 | 1/2011 | Vermaas et al. | |
| 2011/0015096 A1 | 1/2011 | Chiu | |
| 2011/0039732 A1 | 2/2011 | Raymond et al. | |
| 2011/0104785 A1 | 5/2011 | Vaidyanathan et al. | |
| 2011/0105364 A1 | 5/2011 | Kurn | |
| 2011/0129827 A1 | 6/2011 | Causey et al. | |
| 2011/0186466 A1 | 8/2011 | Kurowski et al. | |
| 2011/0189679 A1 | 8/2011 | Kurn et al. | |
| 2011/0224105 A1 | 9/2011 | Kurn et al. | |
| 2011/0288780 A1 | 11/2011 | Rabinowitz et al. | |
| 2011/0294132 A1 | 12/2011 | Kurn | |
| 2011/0319290 A1 | 12/2011 | Raymond et al. | |
| 2012/0003657 A1 | 1/2012 | Myllykangas et al. | |
| 2012/0028310 A1 | 2/2012 | Kurn et al. | |
| 2012/0045797 A1 | 2/2012 | Kurn et al. | |
| 2012/0071331 A1 | 3/2012 | Casbon et al. | |
| 2012/0074925 A1 | 3/2012 | Oliver | |
| 2012/0102054 A1 | 4/2012 | Popescu et al. | |
| 2012/0107811 A1 | 5/2012 | Kelso et al. | |
| 2012/0122701 A1 | 5/2012 | Ryan et al. | |
| 2012/0149068 A1 | 6/2012 | Kurn | |
| 2012/0156728 A1 | 6/2012 | Li et al. | |
| 2012/0157322 A1 | 6/2012 | Myllykangas et al. | |
| 2012/0190587 A1 | 7/2012 | Kurn et al. | |
| 2012/0208705 A1 | 8/2012 | Steemers et al. | |
| 2012/0220479 A1 | 8/2012 | Ericsson et al. | |
| 2012/0220483 A1 | 8/2012 | Kurn et al. | |
| 2012/0220494 A1 | 8/2012 | Samuels et al. | |
| 2012/0237943 A1 | 9/2012 | Soldatov et al. | |
| 2012/0238738 A1 | 9/2012 | Hendrickson | |
| 2012/0245041 A1 | 9/2012 | Brenner et al. | |
| 2012/0252682 A1 | 10/2012 | Zhou et al. | |
| 2012/0270212 A1 | 10/2012 | Rabinowitz et al. | |
| 2012/0283145 A1 | 11/2012 | Wang | |
| 2012/0289426 A1 | 11/2012 | Roos et al. | |
| 2012/0309002 A1 | 12/2012 | Link | |
| 2012/0328487 A1 | 12/2012 | Saito et al. | |
| 2013/0005585 A1 | 1/2013 | Anderson et al. | |
| 2013/0059738 A1 | 3/2013 | Leamon et al. | |
| 2013/0072390 A1 | 3/2013 | Wang et al. | |
| 2013/0137582 A1 | 5/2013 | Ong et al. | |
| 2013/0231253 A1 | 9/2013 | Amorese et al. | |
| 2014/0031240 A1 | 1/2014 | Behlke et al. | |
| 2014/0038188 A1 | 2/2014 | Kurn | |
| 2014/0038236 A1 | 2/2014 | Kurn et al. | |
| 2014/0051585 A1 | 2/2014 | Prosen et al. | |
| 2014/0065692 A1 | 3/2014 | Kurn et al. | |
| 2014/0186827 A1 | 7/2014 | Pieprzyk et al. | |
| 2014/0274729 A1 | 9/2014 | Kurn et al. | |
| 2014/0274731 A1 | 9/2014 | Raymond et al. | |
| 2014/0274738 A1 | 9/2014 | Amorese et al. | |
| 2014/0274741 A1 | 9/2014 | Hunter et al. | |
| 2014/0303000 A1 | 10/2014 | Armour | |
| 2014/0378345 A1 | 12/2014 | Hindson et al. | |
| 2015/0004600 A1 | 1/2015 | Wang et al. | |
| 2015/0011396 A1 | 1/2015 | Schroeder et al. | |
| 2015/0017635 A1 | 1/2015 | Myllykangas et al. | |
| 2015/0037790 A1 | 2/2015 | Fox et al. | |
| 2015/0101595 A1 | 4/2015 | Hancock et al. | |
| 2015/0111208 A1 | 4/2015 | Umbarger et al. | |
| 2015/0133319 A1 | 5/2015 | Fu et al. | |
| 2015/0190802 A1 | 7/2015 | Oppenheimer et al. | |
| 2015/0218620 A1 | 8/2015 | Behlke et al. | |
| 2015/0284769 A1 | 10/2015 | Schroeder | |
| 2015/0299767 A1 | 10/2015 | Armour et al. | |
| 2015/0299784 A1 | 10/2015 | Fan et al. | |
| 2015/0299812 A1 | 10/2015 | Talasaz | |
| 2016/0016140 A1 | 1/2016 | Jovanovich et al. | |
| 2016/0068889 A1 | 3/2016 | Gole et al. | |
| 2016/0122756 A1 | 5/2016 | Armour | |
| 2016/0130576 A1 | 5/2016 | Armour | |
| 2016/0153039 A1 | 6/2016 | Amorese et al. | |
| 2016/0203259 A1 | 7/2016 | Scolnick et al. | |
| 2016/0220994 A1 | 8/2016 | Wright | |
| 2016/0251711 A1 | 9/2016 | Amorese et al. | |
| 2016/0265042 A1 | 9/2016 | Schroeder et al. | |
| 2016/0275240 A1 | 9/2016 | Huelga et al. | |
| 2016/0296930 A1 | 10/2016 | Matear et al. | |
| 2017/0356053 A1 | 12/2017 | Otto et al. | |
| 2018/0127817 A1 | 5/2018 | Borchert et al. | |
| 2018/0216174 A1 | 8/2018 | Shum et al. | |
| 2018/0346977 A1 | 12/2018 | Alt et al. | |

FOREIGN PATENT DOCUMENTS

| | | | |
|---|---|---|---|
| CN | 101565746 A | 10/2009 | |
| CN | 105890722 A | 8/2016 | |
| EP | 0365627 B1 | 12/1993 | |
| EP | 0329822 B1 | 6/1994 | |
| EP | 0667393 A2 | 8/1995 | |
| EP | 1071811 B1 | 3/2002 | |
| EP | 0843735 B1 | 7/2002 | |
| EP | 1362788 A2 | 11/2003 | |
| EP | 2186563 A2 | 5/2010 | |
| EP | 2272976 A1 | 1/2011 | |
| EP | 2322612 A1 | 5/2011 | |
| EP | 2451973 A1 | 5/2012 | |
| EP | 2511381 A2 | 10/2012 | |
| EP | 2538228 A2 | 12/2012 | |
| EP | 2599879 A1 | 6/2013 | |

(56) References Cited

FOREIGN PATENT DOCUMENTS

| | | | |
|---|---|---|---|
| EP | 1929039 | B2 | 11/2013 |
| EP | 2749654 | A1 * | 7/2014 ......... C12N 15/1065 |
| JP | 2015511819 | A | 4/2015 |
| NO | 02/081753 | A1 | 10/2002 |
| WO | 89/09284 | A1 | 10/1989 |
| WO | 92/07951 | A1 | 5/1992 |
| WO | 93/18052 | A1 | 9/1993 |
| WO | 94/16090 | A1 | 7/1994 |
| WO | 96/40998 | A1 | 12/1996 |
| WO | 97/12061 | A1 | 4/1997 |
| WO | 97/25416 | A2 | 7/1997 |
| WO | 98/06736 | A1 | 2/1998 |
| WO | 98/38296 | A1 | 9/1998 |
| WO | 98/044151 | A1 | 10/1998 |
| WO | 99/10540 | A1 | 3/1999 |
| WO | 99/11819 | A1 | 3/1999 |
| WO | 99/42618 | A1 | 8/1999 |
| WO | 00/08208 | A2 | 2/2000 |
| WO | 2000/09756 | A1 | 2/2000 |
| WO | 00/018957 | A1 | 4/2000 |
| WO | 00/39345 | A1 | 7/2000 |
| WO | 2000/043531 | A2 | 7/2000 |
| WO | 00/52191 | A1 | 9/2000 |
| WO | 2000/55364 | A2 | 9/2000 |
| WO | 00/70039 | A1 | 11/2000 |
| WO | 01/20035 | A2 | 3/2001 |
| WO | 01/23613 | A1 | 4/2001 |
| WO | 01/46464 | A1 | 6/2001 |
| WO | 01/57248 | A2 | 8/2001 |
| WO | 01/64952 | A2 | 9/2001 |
| WO | 02/00938 | A2 | 1/2002 |
| WO | 02/28876 | A2 | 4/2002 |
| WO | 02/29117 | A2 | 4/2002 |
| WO | 02/36821 | A2 | 5/2002 |
| WO | 02/48402 | A2 | 6/2002 |
| WO | 02/060318 | A2 | 8/2002 |
| WO | 02/072772 | A2 | 9/2002 |
| WO | 02/072773 | A2 | 9/2002 |
| WO | 02/090584 | A2 | 11/2002 |
| WO | 03/004690 | A2 | 1/2003 |
| WO | 2003/002736 | A2 | 1/2003 |
| WO | 2003/012118 | A1 | 2/2003 |
| WO | 03/022438 | A1 | 3/2003 |
| WO | 03/027259 | A2 | 4/2003 |
| WO | 03/078645 | A2 | 9/2003 |
| WO | 03/083435 | A2 | 10/2003 |
| WO | 03/106642 | A2 | 12/2003 |
| WO | 04/011665 | A2 | 2/2004 |
| WO | 2004/070007 | A2 | 8/2004 |
| WO | 2004/092418 | A2 | 10/2004 |
| WO | 2005/003375 | A2 | 1/2005 |
| WO | 2005/003381 | A1 | 1/2005 |
| WO | 2005/038427 | A2 | 4/2005 |
| WO | 2005/065321 | A2 | 7/2005 |
| WO | 2006/081222 | A2 | 8/2006 |
| WO | 2006/086668 | A2 | 8/2006 |
| WO | 2006/137733 | A1 | 12/2006 |
| WO | 2007/018601 | A1 | 2/2007 |
| WO | 2007/019444 | A2 | 2/2007 |
| WO | 2007/030759 | A2 | 3/2007 |
| WO | 2007/037678 | A2 | 4/2007 |
| WO | 2007/052006 | A1 | 5/2007 |
| WO | 2007/057652 | A1 | 5/2007 |
| WO | 2007/073165 | A1 | 6/2007 |
| WO | 2007/136717 | A1 | 11/2007 |
| WO | 2008/005459 | A2 | 1/2008 |
| WO | 2008/015396 | A2 | 2/2008 |
| WO | 2008/033442 | A2 | 3/2008 |
| WO | 2008/093098 | A2 | 8/2008 |
| WO | 2008/115185 | A2 | 9/2008 |
| WO | 2008150432 | A1 | 12/2008 |
| WO | 2009/053039 | A1 | 4/2009 |
| WO | 2009/102878 | A2 | 8/2009 |
| WO | 2009/102896 | A2 | 8/2009 |
| WO | 2009/112844 | A1 | 9/2009 |
| WO | 2009/117698 | A2 | 9/2009 |
| WO | 2009/120372 | A2 | 10/2009 |
| WO | 2009/120374 | A2 | 10/2009 |
| WO | 2010/003153 | A2 | 1/2010 |
| WO | 2010/030683 | A1 | 3/2010 |
| WO | 2010/039991 | A2 | 4/2010 |
| WO | 2010/063711 | A1 | 6/2010 |
| WO | 2010/064893 | A1 | 6/2010 |
| WO | 2010/085715 | A1 | 7/2010 |
| WO | 2010/091246 | A2 | 8/2010 |
| WO | 2010/115154 | A1 | 10/2010 |
| WO | 2010/129937 | A2 | 11/2010 |
| WO | 2011/003630 | A1 | 1/2011 |
| WO | 2011/009941 | A1 | 1/2011 |
| WO | 2011/019964 | A1 | 2/2011 |
| WO | 2011/032053 | A1 | 3/2011 |
| WO | 2011032040 | A1 | 3/2011 |
| WO | 2011/053987 | A1 | 5/2011 |
| WO | 2011/151777 | A1 | 12/2011 |
| WO | 2011/156529 | A2 | 12/2011 |
| WO | 2012/013932 | A1 | 2/2012 |
| WO | 2012/061832 | A1 | 5/2012 |
| WO | 2012/054873 | A3 | 8/2012 |
| WO | 2012/103154 | A1 | 8/2012 |
| WO | 2013/059740 | A1 | 4/2013 |
| WO | 2013/059746 | A1 | 4/2013 |
| WO | 2013/112923 | A1 | 8/2013 |
| WO | 2013/130674 | A1 | 9/2013 |
| WO | 2013/130512 | A3 | 10/2013 |
| WO | 2013/177220 | A1 | 11/2013 |
| WO | 2013/190441 | A2 | 12/2013 |
| WO | 2013/191775 | A2 | 12/2013 |
| WO | 2014/028778 | A1 | 2/2014 |
| WO | 2014/039556 | A1 | 3/2014 |
| WO | 2014/082032 | A1 | 5/2014 |
| WO | 2013/138510 | A9 | 7/2014 |
| WO | 2014/102397 | A1 | 7/2014 |
| WO | 2014/144092 | A1 | 9/2014 |
| WO | 2014/150931 | A1 | 9/2014 |
| WO | WO-2015019658 | A1 * | 2/2015 .......... C12N 9/1252 |
| WO | 2015/031691 | A1 | 3/2015 |
| WO | 2015/073711 | A1 | 5/2015 |
| WO | 2015/104302 | A1 | 7/2015 |
| WO | 2015/131107 | A1 | 9/2015 |
| WO | 2018/102783 | A1 | 6/2018 |
| WO | 2019/079724 | A1 | 4/2019 |

OTHER PUBLICATIONS

Applied Biosystems, 2010, BigDye Terminator v3.1 Cycle Sequencing Kit Protocol (72 pages).
Baldwin, 2009, Multilocus sequence typing of Cronobacter sakazakii and Cronobacter malonaticus reveals stable clonal structures with clinical significance which do not correlate with biotypes, BMC Microbiol 9(223): 1-9.
Bao, 2014, Review of current methods, applications and data management for the bioinformatics analysis of whole exome sequencing, Cancer Informatics 13:S2, pp. 67-82.
Bellos, 2014, cnvCapSeq: detecting copy number variation in long-range targeted resequencing data, Nucleic Acids Res 42(20):e158.
Benson, 2013, Genbank, Nucl Acids Res 41:D36-D42.
Blomquist, 2013, Targeted RNA-Sequencing with Competitive Multiplex-PCR Amplicon Libraries, PLOS ONE 8(11):e79120.
Bodi, 2013, Comparison of commercially available target enrichment methods for next-generation sequencing, J Biomolecular Tech 24:73-86.
Borodina, 2011, A strand-specific library preparation protocol for RNA sequencing methods, Meth Enzymol 500:79-98.
Browning, 2011, Haplotype phasing: existing methods and new developments, Nature Rev Gen, 12(10):703-714.
Callow, 2004, Selective DNA amplification from complex genomes using universal double-sided adaptors, Nucl Acids Res 32(2):e21/1-6.
Church, 1988, Multiplexed DNA sequencing, Science 240:185-188.
Colbert, 2001, High-throughput screening for induced point mutations, Plant Physiol 126:480-484.

(56) References Cited

OTHER PUBLICATIONS

Collard, 2005, An introduction to markers, quantitative trait loci (QTL) mapping and marker-assisted selection for crop Improvements: the basic concepts Euphytica 142:169-196.

Diao, 2015, Building highly-optimized, low latency pipelines for genomic data analysis, 7th Bienniel Conference on Innovative Data Systems Research (CIDR'15), Jan. 4-7, Asilomar, California, USA, 12 pages.

Eminaga, 2013, Quantification of microRNA Expression with Next-Generation Sequencing, Unit 4.17 in Current Protocols in Molecular Biology, Wiley, New York, NY (14 pages).

Faircloth, 2012, Not all sequence tags are created equal: Designing and validating sequence identification tags robust to indels, PLoSONE 7(8):e42543.

Fakhrai-Rad, 2002, Pyroseqeuncing: An accurate detection platform for single nucleotide polymorphisms, Human Mutation 19:479-485.

Frederico, 1990, A sensitive genetic assay for the detection of cytosine deamination: determination of rate constants and the activation energy, Biochemistry 29(10):2532-2537.

Fromer, 2014, Using XHMM Software to Detect Copy Number Variation in Whole-Exome Sequencing Data, Curr Protoc Hum Genet 81(7.23):1-21.

Fu, 2014, Molecular indexing enables quantitative targeted RNA sequencing and reveals poor efficiencies in standard library preparations, PNAS 111(5):1891-1896 and Supporting Information, 8 pages.

Genereux, 2008, Errors in the bisulfite conversion of DNA: modulating inappropriate and failed conversion frequencies, Nucl Acids Res 36(22):e150.

Gonzales-Beltran, 2015, From Peer-REviewed to Peer-reproduced in scholary publishing: the complementary roles of data models and workflows in Bioinformatics, PLOS ONE 10(7):127612, 23 pages.

Grothues, 1993, PCR amplification of megabase DNA with tagged random primers (T-PCR), Nucl Acids Res 21:1321-1322.

Hajibabaei, 2005, Critical factors for assembling a high vol. of DNA barcodes, Phil Trans R Soc B 360:1959-1967.

Head, 2015, Library construction for next-generation sequencing: Overviews and challenges, Biotechniques 56(2):61.

Illumina, 2011, TruSeq RNA and DNA Sample Preparation Kits v2, 1-15 Illumina, dated Apr. 27, 2011 (4 pages).

Ion Total RNA-Seq Kit v2, User Guide, 2012, Life Technologies (82 pages).

Jiang, 2015, CODEX: a normalization and copy number variation detection method for whole exome sequencing, Nucleic Acids Res 43(6):e39.

John, 2011, Detection of Viral microRNA with S1 Nuclease Protection Assay, Chapter 10 in Antiviral RNAi, van Rig, Ed. Springer.

Kalari et al, MAP-Rseq: Mayo analysis pipeline for RNA sequencing, BMC bioinformatics 2014, vol. 15, 224, 13 pages and Supplemental Information.

Karczewki et al., 2014, STORMSeq: an open-source user-friendly pipleline for processing personal genomics data in the cloud.PLOS ONE 9(1):e84860, 5 pages.

Kim et al., 2011, TopHat-Fusion: an algorithm for discovery of novel fusion transcripts, Cancer Discovery, vol. 12:R72, 15 pages.

Krumm, 2012, Copy number variation detection and genotyping from exome sequence data, Genome Res 22 (8):1525-1532.

Lai, 2004, Characterization of the maize endosperm transcriptome and its comparison to the rice genome, Genome Res14:1932-1937.

Langmead, 2009, Ultrafast and memory-efficient alignment of short DNA sequences to the human genome, Genome Biol 10:R25.

Levin, 2010, Comprehensive comparative analysis of strand-specific RNA sequencing methods, Nat Methods 7(9):709-715.

Li, 2012, CONTRA: copy number analysis for targeted resequencing, Bioinformatics 28(10):1307-1313.

Li, 2014, Bioinformatics pipelines for targeted resequencing and whole-exome sequencing of human and mouse genomes: a virtual appliance approach for instant deployment, PLOS ONE, 9(4):e95217 and Supplemental Information, 11 pages.

Liang, 2014, Copy number variation sequencing for comprehensive diagnosis of chromosome disease syndromes, The Journal of Molecular Diagnostics, 16(5), plus Supplemental Information, 15 pages.

Lindstrom, 2004, Pyrosequencing for detection of Lamivudine-resistant Hepatitis B virus, J Clin Microb 42(10):4788-4795.

Liu, 2008, Sequence space coverage, entropy of genomes and the potential to detect non-human DNA in human samples, BMC Genomics 9(509):1-17.

Ma, 2015, Quantitative Analysis of Copy Number Variants Based on Real-Time LightCycler PCR, Curr Protoc Hum Genet 80:7.21.1-7.23.8.

Machine translation generated Jun. 18, 2021, of JP 2015511819 A (400 pages).

Machine translation generated on Mar. 7, 2018, of CN 105890722 by website of European Patent Office (4 pages).

Margulies, 2005, Genorne sequencing in open microfabricated high density picoliter reactors, Nature 437 (7057):376-380.

Mauk, 2018, Simple Approaches to Minimally-Instrumented, Microfluidic-Based Point-of-Care Nucleic Acid Amplification Tests, Biosensors 8(1):e17.

McCloskey, 2007, Encoding PCR products with batch-stamps and barcodes, Biochem Genet 45:761-767.

Merriman, 2012, Progress in Ion Torrent semiconductor chip based sequencing, Electrophoresis, 35(23):3397-3417.

Miner, 2004, Molecular barcodes detect redundancy and contamination in hairpin-bisulfite PCR, Nucl Acids Res 32 (17):e135, 4 pages.

Morlan, 2012, Selective depletion of rRNA enables whole transcriptome profiling of archival fixed tissue, PLoSOne 7(8):e42882.

Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).

Mühlberger, 2011, Compputational Analysis Workflows for Omics Data Interpretation, In: Mayer B. (eds) Bioinformatics for Omics Data, Methods in Molecular Biology (Methods and Protocols), vol. 719, pp. 379-397, Chapter 17, Humana Press.

NuGEN, 2014, User Guide Ovation Target Enrichment System, NuGEN Technologies Inc., San Carlos, CA (45 pages).

Nugen, 2016, Ovation RNA-Seq User Guide, NuGEN Technologies, Inc., San Carlos, CA (42 pages).

Plagnol, 2012, A robust model for read count data in exome sequencing experiments and implications for copy number variant calling, Bioinformatics 28(21):2747-2754.

Qiu, 2003, DNA sequence-based "bar-codes" for tracking the origins of expressed sequence tags from a maize cDNA library constructed using multiple mRNA sources, Plant Physiol 133:475-481.

Querfurth, 2012, Creation and application of immortalized bait libraries for targeted enrichment and next-generation sequencing, Biotechniques 52(6):375-380.

Ronaghi, 2001, Pyrosequencing sheds light on DNA sequencing, Genome Res 11:3-11.

Rothberg, 2011, An integrated semiconductor device enabling non-optical genome sequencing, Nature 475 (7356):348-352.

Sambrook, 2005, Mapping RNA with nuclease S1, Nat Meth 2:397-398.

Sathirapongsasuti, 2011, Exome sequencing-based copy-number variation and loss of heterozygosity detection: ExomeCNV, Bioinformatics 27(19):2648-2654.

Schiemer, 2011, Illumina TruSeq Adapters Demystified, Tufts University Core Facility XP055357867 (5 pages).

Shapero, 2001, SNP Genotyping by multiplexed solid-phase amplification and fluorescent minisequencing, Genome Res 11:1926-1934.

Shendure, 2005, Accurate multiplex polony sequencing of an evolved bacterial genome, Science 309:1728.

Shiroguchi, 2012, Digital RNA sequencing minimizes sequence dependent bias and amplification noise with optimized single-molecule barcodes, PNAS, 109(4):1347-1352 and Supplemental Information, 22 pages.

(56)        References Cited

OTHER PUBLICATIONS

Smith, 2010, Highly-multiplexed barcode sequencing: an efficient method for parallel analysis of pooled samples, Nucleic Acids Research, 38(13):e142, 7 pages.

Soni, 2007, Progress toward ultrafast DNA sequencing using solid-state nanopores, Clin Chem 53(11):1996-2001.

Sood, 2006, Methods for reverse genetic screening in zebrafish by resequencing and TILLING, Methods 39:220-227.

Staroscik, 2004, Calculator for determining the No. of copies of a template, URI Genomics, webpage archive dated Apr. 6, 2017 (1 page), Retreived from the internet on Mar. 7, 2018, from <https://web.archive.org/web/20170406174850/http://cels.uri.edu/gsc/cndna.html>.

Steffens, 2017, A versatile and low-cost open source pipetting robot for automation of toxicological and ecotoxicological bioassays, PLoS One 12(6):e0179636.

Stratagene, 1998, Gene characterization kits, Stratagene Catalog, p. 39 (2 pages).

Tewhey, 2009, Micrdroplet-based PCR enrichment for large-scall targeted sequencing, Nat Biotech 27(11):1025-1031.

The OVATION Ultralow System V2 User guide, part No. 0344, 0344NB, file name M01379_v5_User_Guide_Ovation_Ultralow_Library_Systems_V2_(Part_No.__0344)_2215.pdf, available from nugen. com from NuGEN Technologies Inc., San Carlos, CA (30 pages).

Till, 2003, Large-scale discovery of induced point mutations with high-throughput TILLING, Genome Res 13:524-530.

Torri, 2012, Next generation sequence analysis and computational genomics using graphical pipeline workflows, Genes, vol. 3, pp. 545-575.

Trapnell, 2010, Transcript assembly and quantification by RNA-Seq reveals unannotated transcripts and isoform switching during cell differentiation, Nat Biotech 28:511-515.

Trapnell, 2013, Differential analysis of gene regulation at transcript resolution with RNA-seq, Nat Biotech 31:46-53.

TRUSEQ Nano DNA Library Prep guide, file name truseq-nano-dna-library-prep-guide-15041110-d.pdf, available from support.illumina.com, Illumina, Inc., San Diego, CA (40 pages).

Tucker, 2009, Massively parallel sequencing: the next big thing in genetic medicine, Am J Human Genet 85:142-154.

Unemo, 2004, Molecular typing of Neisseria gonorrhoeae isolates by pyrosequencing of highly polymorphic segments of the porB gene, J Clin Microb 42(7):2926-2934.

Van der Auwera, 2013, From FastQ data to high confidence variant calls, the Genome Analysis Toolkit Best Practices Pipeline, Current Protocols in Bioinformatics 11.10.1-11.10.33, WileyOnlineLibrary.com, 33 pages.

Vignal, 2002, A review on SNP and other types of molecular markers and their use in animal genetics, Genet Sel Evol 34:275-305.

Wagle, 2012, High-Throughput detection of actionable genomic alterations in clinical tumor samples by targeted massively parallel sequencing, Cancer Discovery, 2(1):82-93.

Walker, 1992, Strand displacement amplification-an isothermal, in vitro DNA amplification technique, Nucl Acids Res 20(7):1691-1696.

Westin 2000, Anchored multiplex amplification on a microelectronic chip array, Nat Biotech 18:199-204.

Wienholds, 2004, Target-selected gene inactivation in zebrafish, Meth Cell Biol 77:69-90.

Wolford, 2000, High-throughput SNP detection by using DNA pooling and denaturing high performance liquid chromatography (DHPLC), Hum Genet 107:483-487.

Xi, 2011, Copy number variation detection in whole-genome sequencing data using the Bayesian information criterion, PNAS 108(46):e1128-e1136.

Xu, 2012, FastUniq: A fast de novo duplicates removal tool for paired short reads, PLoSOne 7(12):e52249.

* cited by examiner

| sample | sample info | total reads | %rRNA |
|--------|-------------|-------------|-------|
| A | with competing rRNA primers | 1,800,778 | 0.87% |
| B | with competing rRNA primers | 1,778,026 | 0.80% |
| C | without competing rRNA primers | 1,739,923 | 44.91% |
| D | without competing rRNA primers | 1,560,111 | 45.03% |

FIG. 3

| Sample | sample info | total reads | %total aligned | 18S rRNA reads | %18S out of total |
|--------|-------------|-------------|----------------|----------------|-------------------|
| A | without cleavable 18S primers | 1,973,647 | 96.6% | 775,191 | 39.3% |
| B | without cleavable 18S primers | 1,890,774 | 96.5% | 751,409 | 39.7% |
| C | with cleavable 18S primers | 1,759,026 | 96.7% | 96,177 | 5.5% |
| C | with cleavable 18S primers | 1,909,053 | 96.7% | 110,546 | 5.8% |

FIG. 4

DEPLETION OF ABUNDANT UNINFORMATIVE SEQUENCES

TECHNICAL FIELD

The invention relates to the preparation of sequencing libraries.

BACKGROUND

RNA sequencing provides important information regarding gene expression and is the bridge between genomics and proteomics. Unfortunately, total RNA preparations usually contain an abundance of uninformative transcripts, such as ribosomal RNA (rRNA) and globin messenger RNA (mRNA). Those sequences have less overall functional relevance, but make up a large proportion of RNA subtypes in, for example, blood samples. Accordingly, any RNA sequence preparation will have substantial "noise" if the intent is to isolate mRNA.

It is therefore desirable to deplete undesirable sequences in RNA-Seq libraries to lower the cost of sequencing and focus results on desired sequence subtypes. Presently, depletion methods such as Ribo-Zero, RiboMinus, and RiboErase are used for that purpose. However, those methods use subtractive hybridization or enzymatic degradation to deplete rRNA prior to library construction. As a result, such techniques are time consuming and can require high RNA input in order to maintain enough relevant RNA for sequencing post-depletion. Current post-library construction depletion methods, such as AnyDeplete and DASH, require multiple steps of enzymatic treatment and purification which are also time consuming.

SUMMARY

Systems and methods of the invention provide cDNA library preparation with integrated depletion of non-desired sequences through the use of sets of primers for selective amplification of desired subsets of RNA over undesired subsets. Selective amplification of transcribed RNA is used to deplete undesired subsets of RNA by a number of different mechanisms as detailed herein. Methods of the invention avoid subtractive hybridization and enzymatic degradation and are therefore more compatible with lower RNA sample input and enable selection of a desired subset of cDNA. In one example, a desired subset of RNA (and therefore cDNA) is mRNA (and its reverse-transcribed cDNA) and undesired subsets include rRNA and globin RNA (and their respective cDNA).

Systems and methods of the invention are compatible with standard cDNA library preparation techniques as well as single primer isothermal amplification (SPIA) techniques. Sequence-specific primers are used in reverse transcription that target non-desired RNA sequences (e.g., rRNA and globin RNA). Those sequence-specific primers may contain a component to prevent further amplification or may lack a component that is required for further amplification. The techniques described herein can be used with whole-transcriptome cDNA synthesis with random primers and without the need for traditional pre or post-library depletion techniques.

In one embodiment, the invention comprises exposing RNA to a first set of random primers that target desired RNA species and a second set of primers that target undesired RNA species. Primers targeting undesired RNA include nucleotide analogs that are incorporated in the resulting cDNA. Those cDNAs are then enzymatically processed to prevent subsequent amplification. The inclusion of an enzymatic treatment step prior to PCR amplification of the transcribed cDNA library results in cleavage or other enzymatic processing of the nucleotide analogs and prevents their subsequent amplification. Because the random amplification-supporting primers lack the nucleotide analogs, they are not affected by the enzymatic processing and subsequent cDNA amplification only amplifies the desired sequences for sequencing or other analysis.

In another embodiment, primers for cDNA synthesis of desired RNA include a tag that is a substrate for amplification primers after reverse transcription. A second set of primers in which the amplification tag is absent targets undesired RNA. One such protocol makes use of single primer isothermal amplification (SPIA) techniques in which an RNA sequence required for SPIA is included in primers targeting desired RNA species but not primers targeting undesired species. Accordingly, SPIA amplification only amplifies the randomly-primed desired sequences, resulting in underrepresentation of the non-desired sequences in the final library.

Aspects of the invention can include a method of preparing a cDNA library by annealing a sequence-specific amplification-suppressing primer to a non-desired RNA fragment in a single-stranded nucleic acid library; annealing an amplification-supporting primer to a desired RNA fragment in the single-stranded nucleic acid library; transcribing the non-desired RNA fragment and the desired RNA fragment to generate a non-desired cDNA molecule comprising an amplification-suppressing sequence and a desired cDNA molecule comprising a amplification-supporting sequence; and selectively amplifying the desired cDNA molecule to generate a cDNA library depleted of non-desired cDNA molecules.

The amplification-supporting primer may include a 5' tag while the amplification-suppressing primer does not and the selectively amplifying step can include amplifying the cDNA library using an amplification primer targeting the 5' tag or its compliment.

The 5' tag may be an RNA tag and the amplification primer is a DNA/RNA chimeric primer. In certain embodiments, the amplification-suppressing primer can include a nucleotide analog and the method may further comprise enzymatically processing the nucleotide analog before the selectively amplifying step to prevent amplification of the non-desired cDNA molecule during the selectively amplifying step. The nucleotide analog may be selected from the group consisting of deoxyuridine (dU) and deoxyinosine (dI). The enzymatically processing step may comprise exposing the nucleotide analog to an enzyme selected from the group consisting of uracil-DNA glycosylase (UDG), endonuclease V (Endo V), apurinic/apyrimidinic endonuclease 1 (APE 1), endonuclease IV (Endo IV), and endonuclease VIII (Endo VIII). In certain embodiments, an archaeal family B DNA polymerase may be used as the amplification enzyme in the cDNA amplification step. dU analogs present in the non-desired cDNA will then stall the archaeal family B DNA polymerase and the amplification of dU marked cDNA will be inhibited. Such a method can be used alone or in combination with the enzymatic processing step.

In various embodiments, the amplification-supporting primer may be a random sequence primer. The cDNA library may be a whole transcriptome cDNA library. The sequence-specific amplification-suppressing primer can target ribosomal RNA (rRNA) such as 28S, 18S, 16S, or 12S rRNA. The sequence-specific amplification-suppressing primer may target globin RNA. Methods of the invention may include sequencing the cDNA library so prepared.

In certain aspects, compositions of the invention may include a RNA sample comprising desired and non-desired RNA fragments; a sequence-specific amplification-suppressing primer targeting a non-desired RNA fragment; an amplification-supporting primer; and a reverse transcriptase.

BRIEF DESCRIPTION OF THE DRAWINGS

FIG. 3 shows sequencing results of a cDNA library prepared as described in Example 1.

FIG. 4 shows sequencing results of a cDNA library prepared as described in Example 2.

DETAILED DESCRIPTION

Figure 1:
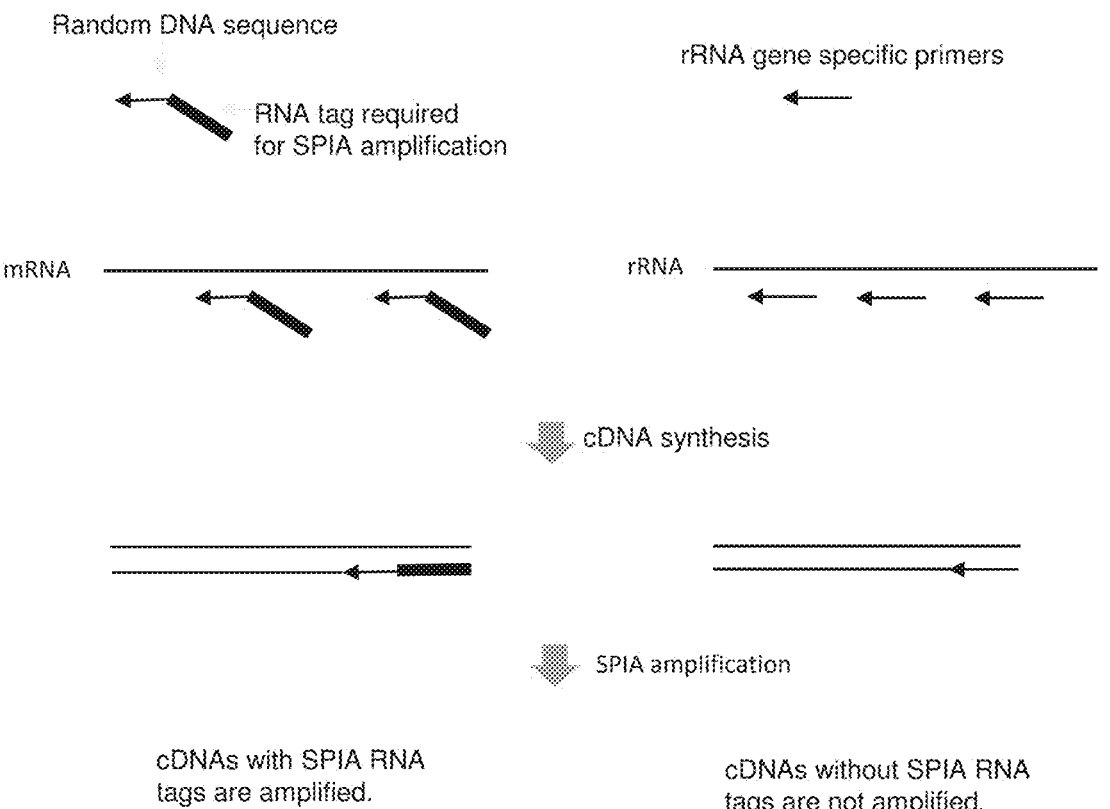
FIG. 1 shows a method of cDNA synthesis using SPIA amplification.

Systems and methods of the invention provide effective depletion of abundant non-informative sequences such as rRNA and globin RNA in whole-transcriptome cDNA synthesis without the requirement for large starting RNA input. The use of two classes of primers during reverse transcription incorporates different sequence tags into different classes of cDNA transcribed therewith. Those different tags may be used for selective amplification during subsequent cDNA library PCR. Accordingly desired cDNA fragments are overrepresented compared to uninformative or non-desired fragments, resulting in effective depletion without the need for subtractive hybridization or enzymatic degradation steps. The resulting streamlined workflow reduces the cost and time of cDNA library preparation relative to existing techniques.

Depletion methods of the invention are compatible with conventional cDNA library preparation protocols as well as those incorporating SPIA amplification steps. For whole-transcriptome analysis the amplification-supporting primers can be random capture unknown sequences and provide diverse representation of the transcriptome.

In traditional techniques the use of random primers in cDNA library preparation results in an abundance of non-desired non-informative sequences because the random primers (as opposed to mRNA targeting oligo dT, for example) do not inherently differentiate between RNA types. The advantage random primers is that the lack of bias in initial reverse transcription allows random priming to capture more transcriptome data than traditional targeted techniques. Instead of positively selecting desired sequences using targeted primers (at the risk of losing valuable sequence information) systems and methods of the invention negatively select uninformative sequences by using primers specifically targeting those non-desired sequences but including sequence tags that permit selective amplification of only the randomly primed cDNA. For example, primers can be sequence-specific for various types of rRNA and the resulting cDNA strands after reverse transcription will include a nucleotide analog that can prevent amplification upon enzymatic processing. In some embodiments, such targeted primers may lack an amplification-supporting sequence, allowing for selective amplification only of the cDNA transcribed using the random primers.

In non-SPIA methods, primers can include nucleotide analogues that, when enzymatically processed, prevent subsequent amplification. Accordingly, the inclusion of a digestion step or other enzymatic process before final cDNA library amplification will result in the selective amplification of only fragments not tagged with the nucleotide analogs.

In cDNA library preparation methods that include SPIA amplification, the RNA sequence required for SPIA can be included in the amplification-supporting primers but absent from the other primers that may be targeted to rRNA or other non-desired fragments. Accordingly when the standard SPIA amplification step is carried out during library preparation, the selectively primed non-desired sequences will not be amplified and therefore be underrepresented in the final cDNA library.

Systems and methods are described herein primarily with reference to cDNA library preparation but one or ordinary skill in the art would appreciate the application of the disclosed primers in augmenting fragment representation in any nucleic acid amplification technique. Such primers can be used not just for RNA in reverse transcription reactions but can be applied to amplification of single and double stranded DNA as well. Initial amplification steps incorporate amplification-supporting sequences only into desired nucleic acid fragments and not into non-desired nucleic acid fragments. Those sequences can be later used to selectively deplete and promote representation of a variety of nucleic acids in amplified libraries.

cDNA libraries are traditionally prepared using an RNA sample (e.g., total RNA or isolated mRNA). RNA can be obtained from a biological sample such as blood, tissue samples, a urine sample, saliva sample, mucus sample, fecal sample, seminal fluid sample, or cerebrospinal fluid sample, either directly or from cells therein. DNase treatment can be used to reduce the amount of genomic DNA. RNA degradation can be checked and total RNA quantified using known methods.

Total RNA is then usually depleted of non-coding rRNA is removed because rRNA represents the vast majority of RNA in a cell (90% or more). Accordingly, the desired, coding sequences could be drowned out in a transcriptome analysis if rRNA is not depleted. Isolated RNA can then be reverse transcribed to cDNA for amplification. By selectively amplifying desired RNA fragments during reverse transcription and amplification, systems and methods of the invention can eliminate the independent depletion methods, saving time and money and avoiding potential loss of desired sequence information.

In cDNA preparation methods as above (lacking a SPIA amplification steps) sequence-specific primers targeting non-desired fragments can be introduced before or during first strand synthesis using reverse transcriptase. The primers can include sequences targeting rRNA or other non-coding RNA and may further include one or more nucleotide analogs susceptible to enzymatic processing that would not affect standard nucleotides. For example such primers may comprise deoxyuridine (dU) or deoxyinosine (dI).

Figure 2:
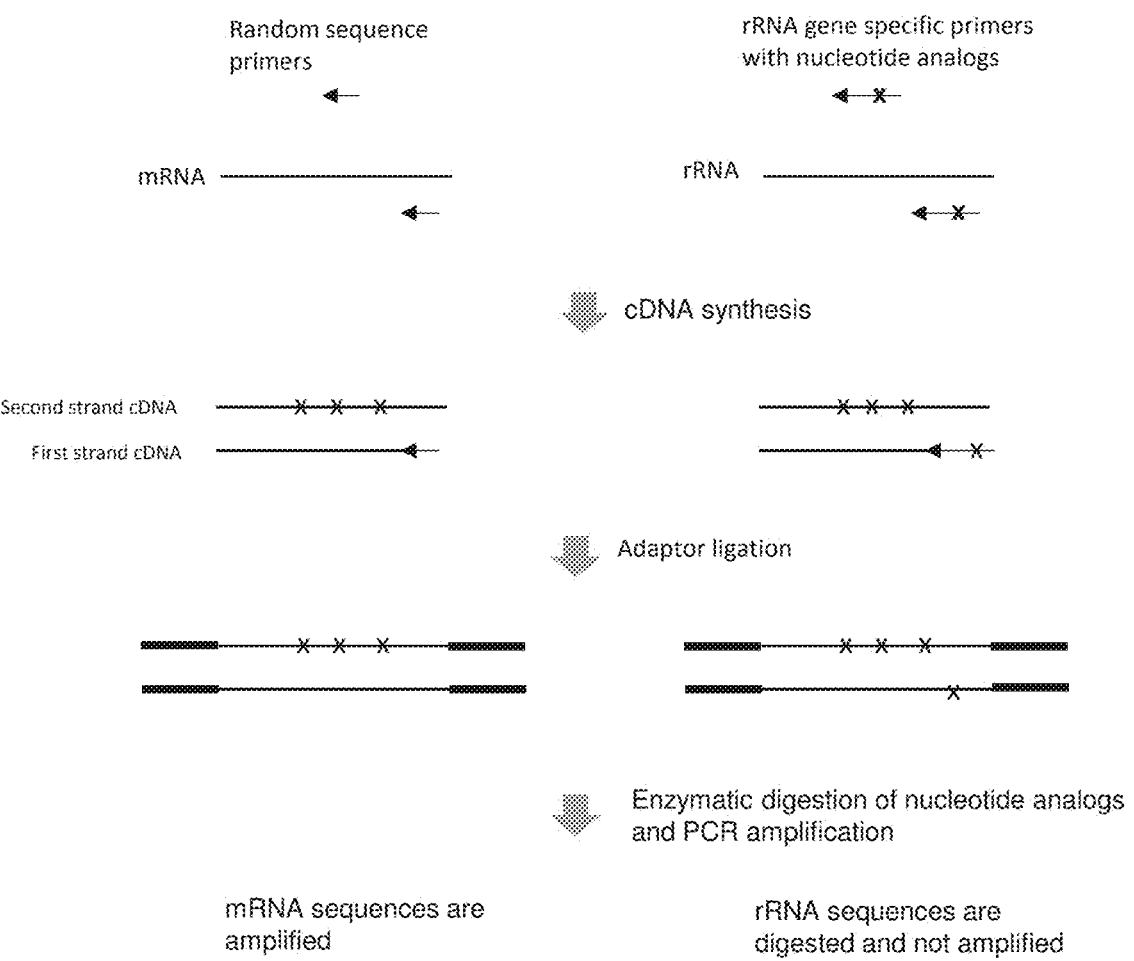
FIG. 2 shows a method of cDNA synthesis without SPIA amplification.

After transcription and before or during cDNA amplification, the nucleotide analogs can enzymatically processed through the inclusion of an enzyme such as uracil-DNA glycosylase (UDG), endonuclease V (Endo V), apurinic/apyrimidinic endonuclease 1 (APE 1), endonuclease IV (Endo IV), or endonuclease VIII (Endo VIII). Such enzymes may selectively target the nucleotide analogs present only in the non-desired fragments, thereby rendering only those fragments not amplifiable. Subsequent standard library amplification techniques will therefore only amplify the desired sequences, effectively depleting the final cDNA library of non-desired sequences. Selective suppression of non-desired sequences in non-SPIA cDNA library preparation is depicted in FIG. 2.

Single primer isothermal amplification, or SPIA is a cDNA library preparation technique used in various RNA-Seq systems such as the Ovation RNA-Seq System available from Tecan Group Ltd. (Switzerland). See U.S. Pat. Pub. 2004/0023271, incorporated herein by reference. SPIA can be used to generate amplified cDNA from small amounts of total RNA (e.g., as little as 500 pg). First strand cDNA is prepared from total RNA using a unique first strand DNA/RNA chimeric primer mix and reverse transcriptase (RT). The primers have a DNA portion that hybridizes either to the 5' portion of the poly(A) sequence or randomly across the transcript. RT extends the 3' DNA end of each primer generating first strand cDNA. The resulting cDNA/mRNA hybrid molecule contains a unique RNA sequence at the 5' end of the cDNA strand.

DNA/RNA Heteroduplex Double-stranded cDNA is then generated. Fragmentation of the mRNA within the cDNA/mRNA complex creates priming sites for DNA polymerase to synthesize a second strand, which includes DNA complementary to the 5' unique sequence of the first strand chimeric primers. The result is a double-stranded cDNA with a unique DNA/RNA heteroduplex at one end.

SPIA amplification is then performed using a DNA/RNA chimeric SPIA primer, DNA polymerase and RNase H in a homogeneous isothermal assay that provides highly efficient amplification of DNA sequences. RNase H is used to degrade RNA in the DNA/RNA heteroduplex at the 5' end of the first cDNA strand. This results in the exposure of a DNA sequence that is available for binding the first SPIA primer. DNA polymerase then initiates replication at the 3' end of the primer, displacing the existing forward strand. The RNA portion at the 5' end of the newly synthesized strand is again removed by RNase H, exposing part of the unique priming site for initiation of the next round of cDNA synthesis. The process of SPIA DNA/RNA primer binding, DNA replication, strand displacement and RNA cleavage is repeated, resulting in rapid accumulation of SPIA cDNA.

Depletion systems and methods of the invention use a combination primer classes in the initial first strand synthesis. While one set of primers have the unique RNA sequence as in the standard SPIA technique described above, another set of primers may be included targeting sequences specific to non-desired RNA (e.g., rRNA or globin RNA) and, importantly, lacking the unique RNA sequence. The transcription products then consist of desired, randomly primed cDNA/mRNA hybrid molecules containing a unique RNA sequence at the 5' end of the cDNA strand and targeted non-desired sequences lacking that unique RNA sequence.

The subsequent SPIA amplification steps are performed as described above and, while the desired cDNA molecules present the binding site for the SPIA primer, the non-desired sequences lacking the binding site are not recognized by the SPIA primer and are therefore not replicated. Accordingly, after amplification, a cDNA library is obtained in which the non-desired sequences (e.g., those derived from rRNA and globin RNA) are underrepresented. The resulting cDNA library can be analyzed without further depletion. Systems and methods of the invention are not incompatible with traditional depletion techniques and, in certain embodiments, depletion techniques such as Ribo-Zero (Illumina, Inc.), RiboMinus (Thermo Fisher Scientific), RiboErase (Kapa Biosystems, Inc.), AnyDepelete (Tecan Group Ltd.), and DASH (See U.S. Pat. Pub. 2018/0051320, incorporated herein by reference) may be combined with the present methods. Depletion of non-desired sequences in cDNA library preparation with SPIA amplification is depicted in FIG. 1.

As described herein, primers may target non-desired sequences. For example, such primers may target sequences specific to rRNA or globin RNA. One of ordinary skill in the art would understand the standard processes of sequence analysis and primer design using available tools to identify target sequences specific to non-desired RNA and synthesize primers targeting those sequences. In certain embodiments, primers specific to 28S, 18S, 16S, and 12S rRNA may be added to first strand synthesis reactions to reduce the representation of unwanted rRNA sequences in the final cDNA library.

As noted above, nucleic acid libraries prepared using the methods described herein can be subjected to subsequent analysis. For example, systems and methods of the invention have beneficial applications in cDNA library synthesis for whole transcriptome sequencing. Accordingly, after cDNA library preparation using the techniques described herein, standard sequencing and sequence analysis methods known in the art including traditional Sanger sequencing methods or next-generation sequencing (NGS) methods. NGS generally refers to non-Sanger-based high throughput nucleic acid sequencing technologies, in which many (i.e., thousands, millions, or billions) of nucleic acid strands can be sequenced in parallel. Examples of such NGS sequencing includes platforms produced by Illumina (e.g., HiSeq, MiSeq, NextSeq, MiniSeq, and iSeq 100), Pacific Biosciences (e.g., Sequel and RSII), and Ion Torrent by ThermoFisher (e.g., Ion S5, Ion Proton, Ion PGM, and Ion Chef systems). It is understood that any suitable NGS sequencing platform may be used for NGS to sequence nucleic acid libraries prepared using the methods described above. Due to the underrepresentation of non-desired sequences, sequencing and analysis costs and complexity are reduced and, in the case of RNA seq, more accurate and reliable transcriptome data can be obtained.

EXAMPLES

Example 1: —cDNA Library Preparation with SPIA Amplification

Libraries were constructed using 5 ng of K562 total RNA and reagents from the Trio RNA-Seq Library Preparation Kit (Tecan Group, Ltd.) following the following steps. The sample was treated with DNase. First strand cDNA synthesis was carried out with 254 primers lacking the SPIA RNA tag and specific to 28S, 18S, 16S, and 12S rRNA at 120 nM each in addition to standard first strand cDNA synthesis reagents from the Trio kit.

Second strand cDNA synthesis was performed as standard followed by standard cDNA purification and SPIA amplification per the kit protocol. After fragmentation and end repair, adaptor ligation, adapter ligation purification, library amplification, and purification, all according to standard kit protocol, the libraries were sequenced on an Illumina MiSeq sequencer. The sequencing results are shown in FIG. 3.

Example 2: Traditional cDNA Library Preparation

Libraries were constructed using 100 ng of K562 total RNA and reagents from the Universal Plus mRNA-Seq Library Preparation Kit (Tecan Group, Ltd.) using the following protocol steps.

RNA was fragmented in a mixture of 10 µL of Fragmentation buffer, 2 µL of 50 ng/µL K562 total RNA, 6.5 µL of water, and 1.5 µL of 81 primers specific to 18S rRNA at 0.5 µM each. The mixture was incubated at the following temperatures and intervals 94 C-5 min, 75 C-2 min, 70 C-2 min, 65 C-2 min, 60 C-2 min, 55 C-2 min, 37 C-5 min, 25 C-5 min, 4 C-hold to promote annealing of the 18S rRNA primers. First strand and second strand synthesis was performed using the standard Universal Plus mRNA-Seq Library Preparation Kit protocol.

After standard cDNA purification, end repair, adaptor ligation, strand selection, strand selection purification, library amplification, and purification, the libraries were sequenced on an Illumina MiSeq sequencer. The results are shown in FIG. 4.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of preparing a cDNA library, the method comprising:
   (i) providing RNA obtained from a sample, said RNA comprising a targeted subset of RNA sequences and a non-target subset of RNA sequences;
   (ii) providing a first set of primers, wherein primers of the first set of primers are specific for the non-target subset of RNA sequences;

providing a second set of primers, wherein primers of the second set of primers are random primers or target-specific primers for the target subset of RNA wherein said second set of primers comprise a 5' RNA tag,
   (iii) transcribing the RNA into cDNA using the first and second set of primers;
   (iv) selectively amplifying the cDNA transcribed from the targeted subset of RNA using the second set of primers thereby generating a cDNA library comprising amplicons from only said target subset of RNA, wherein the selectively amplifying step comprises amplifying the cDNA using an amplification primer targeting the 5' tag or its compliment, wherein the amplification primer is a DNA/RNA chimeric primer,
   wherein generating the cDNA library comprising amplicons from only said target subset of RNA does not include subtractive hybridization or enzymatic degradation of cDNA transcribed using the first set of primers.

2. The method of claim 1 wherein the amplifying step comprises amplifying the cDNA using an archaeal family B DNA polymerase.

3. The method of claim 1 wherein the cDNA library is a whole transcriptome cDNA library.

4. The method of claim 1 wherein the first set of primers target ribosomal RNA (rRNA).

5. The method of claim 4 wherein the first set of primers target 28S, 18S, 16S, or 12S rRNA.

6. The method of claim 1 wherein the first set of primers target globin RNA.

7. The method of claim 1 further comprising sequencing the cDNA library.

8. The method of claim 1, wherein the second set of primers are target-specific primers for the target subset of RNA.

9. The method of claim 1, wherein the 5' tag comprises RNA and the cDNA amplification primer is a DNA/RNA chimeric single primer isothermal amplification (SPIA) primer.

10. The method of claim 9, wherein the selective amplification is a single primer isothermal amplification.

* * * * *